United States Patent
Shelly, Jr. et al.

(10) Patent No.: US 7,666,686 B2
(45) Date of Patent: Feb. 23, 2010

(54) METHOD FOR SAMPLE PREPARATION BY SOLID PHASE EXTRACTION

(75) Inventors: Donald L. Shelly, Jr., Lewistown, PA (US); Phillip Spraker, Max Meadows, VA (US); William L. Ozanich, Jr., Reedsville, PA (US); Michael J. Telepchak, Yardley, PA (US)

(73) Assignee: United Chemical Technologies, Inc., Bristol, PA (US)

( * ) Notice: Subject to any disclaimer, the term of this patent is extended or adjusted under 35 U.S.C. 154(b) by 508 days.

(21) Appl. No.: 11/434,270

(22) Filed: May 15, 2006

(65) Prior Publication Data

US 2007/0264724 A1   Nov. 15, 2007

(51) Int. Cl.
    *G01N 1/18* (2006.01)
(52) U.S. Cl. .................. 436/178; 436/177; 436/181
(58) Field of Classification Search ........... 436/177, 436/178, 181
    See application file for complete search history.

(56) References Cited

U.S. PATENT DOCUMENTS

| | | | |
|---|---|---|---|
| 5,260,028 A | 11/1993 | Astle | 422/81 |
| 5,612,002 A | 3/1997 | Cody et al. | 422/131 |
| 6,277,648 B1 * | 8/2001 | Colpan | 436/177 |
| 6,495,375 B2 * | 12/2002 | Ledig | 436/181 |
| 6,541,273 B1 * | 4/2003 | Plaisance | 436/178 |
| 2004/0013572 A1 | 1/2004 | Moore et al. | 422/99 |
| 2005/0252859 A1 | 11/2005 | Hofmann et al. | 210/656 |

OTHER PUBLICATIONS

United Chemical Technologies, Inc, "Enviroclean Catalogue" (2006) pp. 1-62.
United Chemical Technologies, Inc., "Solid Phase Extraction Applications Manual" (2006), pp. 1-63.
Calgon Carbon Corporation, "Activated Carbon Filters for Indoor Air Quality", (2006).
Calgon Carbon Corporation, "Air Purification Systems" (2004).
D. White et al.,: "What is Clean, Dry, Air?" Technical Article Program TAP106Compressed Air and Gas Institute, (2002).
P.J. Beney et al., "Review, Evaluation, and Application of Solid Phase Extraction Methods", *University Hygienic Laboratory*, University of Iowa, 35(6): 1-5 (1996).
P. Loconto, "Trace Environmental Quantitative Analysis: Principles, Techniques, and Applications", Second Edition, CRC Press, 2006.
N. Simpson (Ed.), "Solid-Phase Extraction: Principles, Techniques, and Applications" pp. 1-38, 97-123, 125-182, 243-271, Marcel Dekker, 2000.
T. C. Dickenson, "Filters and Filtration Handbook", pp. 623-771, 4$^{th}$ Edition, Elsevier, 1997.

* cited by examiner

*Primary Examiner*—Jill Warden
*Assistant Examiner*—Dwan A Gerido
(74) *Attorney, Agent, or Firm*—Drinker Biddle & Reath LLP

(57) ABSTRACT

An method for sample preparation using solid phase extraction. Using an apparatus comprising a SPE cartridge and a sorbent-containing gas filter which contains a sorbent and is detachably connected to the SPE cartridge the gas used to dry the SPE cartridge is purified by passage through the gas filter, thereby preventing contamination of the SPE sorbent by airborne contaminants.

21 Claims, 1 Drawing Sheet

METHOD FOR SAMPLE PREPARATION BY SOLID PHASE EXTRACTION

FIELD OF THE INVENTION

The invention relates to a method for sample preparation for chemical analysis using solid phase extraction.

BACKGROUND OF THE INVENTION

The sample preparation process has a direct impact on accuracy, precision, and quantitation limits and is often the rate determining step for many analytical methods. For example, in environmental analysis, the analytes are present in only trace quantities in solution, and dilute aqueous samples must be processed in order to isolate and concentrate analytes from the sample matrix and provide a suitable sample extract for instrumental analysis. Sample preparation is arguably the most important step in the analytical process. Analytical chemists therefore continue to search for sample preparation procedures that are faster, easier, safer, and less expensive to perform yet provide accurate and precise data with reasonable quantitation limits.

Solid phase extraction (SPE) techniques have replaced many methods for the determination of organic analytes in aqueous samples. SPE methods use solid sorbents which are typically packed into disposable plastic or glass cartridges. When a liquid sample containing analytes is passed through a bed of solid phase sorbent, the analytes are retained on the sorbent and thereby separated from the liquid. Subsequently, the analytes can be eluted from the sorbent by using a relatively small volume of a suitable solvent, whereby a relatively concentrated solution of the analytes can be obtained, and the resulting solution can be subjected to suitable instrumental analysis techniques in order to identify and/or quantitate the analytes that were present, possibly in trace amounts, in the original liquid sample.

Conducting the SPE sample preparation typically involves at least three steps: (1) eluting the liquid sample through the bed of solid phase sorbent to extract the analytes; (2) drying the sorbent by passing nitrogen, or other inert gas, or air through the sorbent bed; and (3) eluting the analytes from the sorbent bed using a suitable solvent.

The sorbent must be completely dried before the samples are eluted, typically with an organic solvent, to obtain the solution of analytes for instrumental analysis. This is typically achieved by passing an air or inert gas flow through the sorbent bed. However, particularly when aqueous samples are being analyzed, drying takes a long time. For example, with a typical SPE cartridge, it generally takes about five to twenty minutes or longer to dry the cartridge completely. During the drying process a large amount of air or nitrogen is passed through the sorbent.

Use of nitrogen, or another bottled inert gas, is one option for drying the sorbent bed. However, providing the supply of pressurized inert gas such as nitrogen is very inconvenient and expensive. Typically, the gases are supplied at high pressure—over 2000 p.s.i.—in large, heavy, metal cylinders weighing over 150 pounds that can be difficult and hazardous to move and store. Laboratories typically must pay both to rent the cylinder and purchase the gas. Because of the large amount of gas often required to dry the sorbent bed, the cylinders are quickly exhausted of nitrogen and must be refilled, which is both inconvenient and expensive. Unless expensive, high quality, "purity assured" gas is used, the cylinders may be contaminated, and the contaminants from the gas may be adsorbed onto the solid phase sorbent and interfere with the analysis. Even if the highest quality, most expensive, inert gas is used, another problem that must be overcome is potential contamination of laboratory equipment; for example, in the tubing connecting the inert gas supply to the SPE cartridge. In addition, inert gases such as nitrogen are asphyxiant, so care must be taken to provide adequate ventilation if large amounts of the inert gas are being released.

On the other hand, although using air to dry the sorbent is inexpensive, convenient, and safe, a significant problem occurs because of the large volume of air required by the drying process. Contaminants present in the air used to dry the sorbent can be adsorbed onto the sorbent, and interfere with the analysis. Since the analytes may be present in only trace quantities in the liquid samples being analyzed, contaminants adsorbed from the air can interfere significantly with the analysis. This may be exacerbated in a laboratory setting where chemicals, possibly including standard samples of the analytes of interest, may be being used, and therefore may be present in the laboratory air.

An apparatus and method is therefore needed to enable SPE sorbents to be inexpensively and conveniently dried, which avoid the expense, inconvenience and hazards associated with using bottled inert gas, but also avoid the problems with contamination by airborne contaminants that can be observed when air is used to dry the sorbents.

BRIEF DESCRIPTION OF THE INVENTION

We provide a new method for sample preparation for analysis of liquid samples comprising:

providing a solid phase extraction cartridge which comprises a first container having an inlet and an outlet and containing a bed of a first sorbent;

providing a gas filter which comprises a second container having an inlet and an outlet and containing a bed of a second sorbent;

introducing a liquid sample into the solid phase extraction cartridge, such that the liquid sample is not passed through the bed of the second sorbent before being introduced into the solid phase extraction cartridge;

passing the liquid sample through the bed of the first sorbent;

with an essentially gastight connection formed between the outlet of the gas filter and the inlet of the solid phase extraction cartridge, passing a gas through the gas filter and the solid phase extraction cartridge such that the gas passes through the bed of the second sorbent in the gas filter before passing through the bed of the first sorbent in the solid phase extraction cartridge to dry the bed of the first sorbent;

introducing a solvent into the solid phase extraction cartridge, such that the solvent is not passed through the bed of the second sorbent before being introduced into the solid phase extraction cartridge;

passing the solvent through the dried bed of the first sorbent; and collecting the solvent after passage through the bed of the first sorbent.

In some embodiments of the invention, the bed of the first sorbent is contained in a volume defined by two porous filters positioned between the inlet and outlet of the solid phase extraction cartridge and the bed of the second sorbent is contained in a volume defined by two porous filters positioned between the inlet and outlet of the gas filter.

In some embodiments of the invention, the first and second containers are cylindrical tubes each having a luer fitting at its outlet and each also having one of the porous filters adjacent to its outlet.

A preferred embodiment of the apparatus used in the method of the invention further comprises an adapter so dimensioned as to form a tight fit to the inlet of the solid phase extraction cartridge and receive the luer fitting of the outlet of the gas filter, the adapter thereby forming the essentially gastight connection between the inlet of the solid phase extraction cartridge and the outlet of the gas filter.

Embodiments of the invention include those in which the first sorbent comprises at least one composition selected from the group consisting of silica; bonded silicas; silicates; alumina; activated carbon; graphitized carbon; and ion exchange resins.

In particular embodiments of the invention, the first sorbent comprises at least one composition selected from the group consisting of unbonded silica; octadecyl bonded silica; octyl bonded silica; ethyl bonded silica; propyl bonded silica, n-butyl bonded silica, isobutyl bonded silica, tertiary butyl bonded silica, pentyl bonded silica, hexyl bonded silica; heptyl bonded silica; n-decyl bonded silica; n-dodecyl bonded silica; eicosyl bonded silica; tricontyl bonded silica; phenyl bonded silica; cyclohexyl bonded silica; cyanopropyl bonded silica; propanediol bonded silica; diethylaminoethyl bonded silica; aminopropyl bonded silica; carboxyethyl bonded silica; propylsulfonic acid bonded silica; ethylbenzene sulfonic acid bonded silica; cyanopropyl bonded silica; trimethylammonium propyl bonded silica; magnesium silicate; acidic alumina; basic alumina; neutral alumina; activated carbon; and graphitized carbon.

In preferred embodiments of the invention, the first sorbent comprises a bonded silica.

Embodiments of the invention include those wherein the second sorbent comprises at least one composition selected from the group consisting of silica; bonded silicas; silicates; alumina; activated carbon; graphitized carbon; and ion exchange resins.

In particular embodiments of the invention, the second sorbent comprises at least one composition selected from the group consisting of unbonded silica; octadecyl bonded silica; octyl bonded silica; ethyl bonded silica; propyl bonded silica, n-butyl bonded silica, isobutyl bonded silica, tertiary butyl bonded silica, pentyl bonded silica, hexyl bonded silica; heptyl bonded silica; n-decyl bonded silica; n-dodecyl bonded silica; eicosyl bonded silica; tricontyl bonded silica; phenyl bonded silica; cyclohexyl bonded silica; cyanopropyl bonded silica; propanediol bonded silica; diethylaminoethyl bonded silica; aminopropyl bonded silica; carboxyethyl bonded silica; propylsulfonic acid bonded silica; ethylbenzene sulfonic acid bonded silica; cyanopropyl bonded silica; trimethylammonium propyl bonded silica; magnesium silicate; acidic alumina; basic alumina; neutral alumina; activated carbon; and graphitized carbon.

In preferred embodiments of the invention, the second sorbent comprises activated carbon, most preferably granular activated carbon.

In other preferred embodiments of the invention, the bed of the second sorbent comprises a first layer comprising activated carbon, preferably granular activated carbon, and a second layer comprising silica.

Other particular embodiments are those wherein the weight of the sorbent in the gas filter is about two times or more, preferably about five times or more, the weight of the sorbent in the solid phase extraction cartridge.

Other particular embodiments of the invention include those wherein the liquid sample is a water sample.

Preferred embodiments of the invention include those wherein the gas is air, preferably unpurified ambient air.

In one embodiment of the invention, the gas is passed through the connected gas filter and solid phase extraction cartridge by applying positive pressure of gas at the inlet of the gas filter.

In another embodiment of the invention air is passed through the connected gas filter and solid phase extraction cartridge by applying suction at the outlet of the solid phase extraction cartridge.

DETAILED DESCRIPTION OF THE INVENTION

Figure 1:
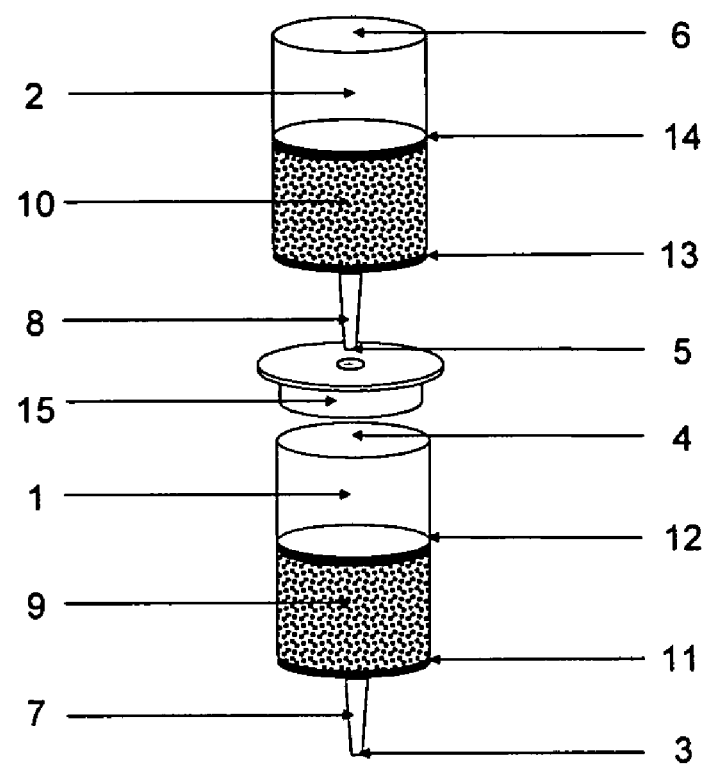
FIG. 1 shows a preferred embodiment of the apparatus used in the method of the invention.

One factor that laboratories have little of no control over is the quality of the laboratory air. During SPE extraction, air is pulled through the SPE sorbent to remove any moisture prior to elution. If the laboratory air contains contaminants such as organic compounds which have an affinity for the sorbent, these compounds will adsorb onto the sorbent and will be extracted along with the sample resulting in contamination. The apparatus of the invention solves this problem by providing a gas filter containing a second bed of sorbent which is attached to the container containing the SPE sorbent during the drying process. Air is passed through the SPE sorbent only after first passing through a bed of sorbent in the filter. The bed of sorbent in the filter absorbs airborne contaminants, thereby preventing the airborne contaminants from contaminating the analytes on the SPE sorbent.

The method of the invention uses an apparatus which comprises a combination of an SPE cartridge and a gas filter. The SPE cartridge comprises a container having an inlet and an outlet which contains a bed of a first sorbent. The gas filter comprises a second container, also with an inlet and an outlet, which contains a bed of a second sorbent. The containers can be made of a variety of materials. The material of the first container is preferably selected to be compatible with a wide variety of solvents that may be used with the SPE cartridge, either as a component of the solutions for analysis, or used in conditioning, washing, or eluting material from the sorbent. Examples of suitable materials include polypropylene and glass. Polypropylene is preferred. The volume of the containers depend on the analytical application for which the apparatus is to be used, and depends on the amount of sorbent required, as well as the sample volumes involved. For example, for convenient operation the SPE cartridge container should be large enough to accommodate the sample as well as the adsorbent. Typical container volumes range from about 1 ml to about 100 ml, for example 1 ml, 3 ml, 6 ml, 10 ml, 15 ml, 30 ml, 25 ml and 75 ml.

The beds of sorbent in the SPE cartridge and the gas filter can be retained in the containers by a variety of means. For example, the sorbent can be emeshed in a web of PTFE or other inert material, or trapped in a glass fibre or paper filter. In a preferred embodiment of the invention, the beds of sorbent in the SPE cartridge and the gas filter are contained in volumes defined by two porous filters positioned between the inlet and outlet of each container. The porous filters or frits could be any of a variety of materials in which the pores are sufficiently large to allow the liquid sample and gas to pass quite readily, but sufficiently small to retain the sorbent. The material of the filter is preferably selected to be compatible with a wide variety of solvents that may be used with the apparatus, either as a component of the solutions for analysis, or used in conditioning, washing, or eluting material from the sorbent. Examples of suitable materials include polyethylene, polypropylene, PTFE, stainless steel, and glass. Polyethylene is preferred.

The containers which form the SPE cartridge and the gas filter in principle could take a variety of forms. In a preferred embodiment of the invention, the containers have a syringe-barrel-like form, being cylindrical tubes with a luer fitting at the outlet at the bottom of the tube, with one of the porous filters also at the bottom of each tube adjacent to the outlet which is equipped with the luer fitting.

An essentially gastight connection is formed between the outlet of the gas filter and the inlet of the SPE cartridge. This essentially gastight connection can be formed in a number of ways; for example, by opening or closing valves, or by connecting tubing between the containers. In a preferred embodiment, the outlet of the air filter can be attached to the inlet of the solid phase extraction cartridge. Optionally, and preferably, the connection is detachable so that the same inlet of the solid phase extraction cartridge can be used to introduce both the liquid sample and the filtered gas to dry the solid phase extraction cartridge. For example the outlet of the SPE cartridge and outlet of the gas filter can be dimensioned so that a tight fit is formed when the two are brought together. Another preferred embodiment of the invention provides an adapter which is dimensioned so as to form a gastight fit between the filter and the SPE cartridge. In the embodiment where the SPE cartridge and gas filter take the form of cylindrical tubes with a luer fitting at the outlet, the adapter takes the form of a tightly fitting lid for the SPE cartridge with a hole having complementary dimensions to those of the luer fitting of the gas filter. The gastight connection between the SPE cartridge and filter is then formed by placing the adapter on the SPE cartridge, and inserting the luer fitting of the gas filter into the hole in the adapter.

FIG. 1 illustrates the preferred apparatus used for the method of the invention. The SPE cartridge 1 and gas filter 2 are shown. The SPE cartridge and the gas filter comprise tubes (containers) 1 and 2 respectively, each with inlets 4 and 6, and outlets 3 and 5. In the preferred embodiment, the containers are provided with luer tips 7 and 8. The SPE cartridge and gas filter each contain a bed of sorbent 9 and 10, respectively. In the preferred embodiment, the sorbent is retained in each tube by means of porous filters 11, 12, 13, and 14. An essentially gastight detachable connection between the tubes is formed, in the preferred embodiment, using an adapter 15 which is dimensioned to form a tight fit into the inlet 4 of the SPE cartridge, and has a hole to receive the luer tip 8 at the outlet of the gas filter.

A wide variety of sorbents can be used in both the SPE cartridge and the filter. The examples mentioned below are intended to be illustrative and not limiting.

The selection of the sorbent for use in the SPE cartridge depends on the particular analytical application for which the SPE cartridge is intended to be used. The sorbent selected will be one that adsorbs the analytes from the solution to be analyzed, but also permits the analytes to be eluted from the cartridge with a suitable solvent or solution after the solution to be analyzed has been passed through the cartridge and the sorbent has been dried. For optimal performance, the sorbent may comprise a single composition or a mixture of more than one composition. If more than one sorbent composition is used, the sorbent compositions may be mixed together or arranged in layers in the bed, for example two, three, or four layers, of different sorbent composition. Classes of sorbents that are used for SPE include: silica; bonded silicas; silicates; alumina; activated carbon; graphitized carbon; and ion exchange resins. Particular examples of sorbents which may be used in the SPE cartridge include: unbonded silica; octadecyl bonded silica; octyl bonded silica; ethyl bonded silica; propyl bonded silica, n-butyl bonded silica, isobutyl bonded silica, tertiary butyl bonded silica, pentyl bonded silica, hexyl bonded silica; heptyl bonded silica; n-decyl bonded silica; n-dodecyl bonded silica; eicosyl bonded silica; tricontyl bonded silica; phenyl bonded silica; cyclohexyl bonded silica; cyanopropyl bonded silica; propanediol bonded silica; diethylaminoethyl bonded silica; aminopropyl bonded silica; carboxyethyl bonded silica; propylsulfonic acid bonded silica; ethylbenzene sulfonic acid bonded silica; cyanopropyl bonded silica; trimethylammonium propyl bonded silica; magnesium silicate; acidic alumina; basic alumina; neutral alumina; activated carbon; and graphitized carbon. The amount of sorbent used in the SPE cartridge will depend on the analytical application for which the apparatus is intended to be used. Typical amounts, which are stated by way of illustration, and are not intended to limit the scope of the invention, range from about 10 mg to about 50000 mg, preferably 50 mg to 10000 mg, for example 50, 100, 200, 500, 1000, 2000, 5000, or 10000 mg. Particle sizes of the sorbent used in the SPE cartridge depend on the material and application. Typically, average particle sizes, which are stated by way of illustration, and are not intended to limit the scope of the invention, are in the range of about 5 to about 210 µm, most typically about 40 to about 60 µm.

The selection of the sorbent for use in the gas filter similarly depends on the particular analytical application for which the SPE cartridge is intended to be used. The sorbent selected will be one that efficiently removes contaminants from the gas which passes through the filter. For optimal efficiency, the sorbent may comprise a single composition or a mixture of more than one composition. If more than one sorbent composition is used, the sorbent compositions may be mixed together or arranged in layers in the bed, for example two, three, or four layers, of different sorbent composition. Examples of classes of sorbents that may be used either alone, or in combination with other sorbents, include silica; bonded silicas; silicates; alumina; activated carbon; graphitized carbon; and ion exchange resins. Particular examples of sorbents which may be used in the filter include: unbonded silica; octadecyl bonded silica; octyl bonded silica; ethyl bonded silica; propyl bonded silica, n-butyl bonded silica, isobutyl bonded silica, tertiary butyl bonded silica, pentyl bonded silica, hexyl bonded silica; heptyl bonded silica; n-decyl bonded silica; n-dodecyl bonded silica; eicosyl bonded silica; tricontyl bonded silica; phenyl bonded silica; cyclohexyl bonded silica; cyanopropyl bonded silica; propanediol bonded silica; diethylaminoethyl bonded silica; aminopropyl bonded silica; carboxyethyl bonded silica; propylsulfonic acid bonded silica; ethylbenzene sulfonic acid bonded silica; cyanopropyl bonded silica; trimethylammonium propyl bonded silica; magnesium silicate; acidic alumina; basic alumina; neutral alumina; activated carbon; and graphitized carbon. In a preferred embodiment, the sorbent comprises activated carbon, preferably granulated activated carbon. In another preferred embodiment, the sorbent bed comprises a layer comprising activated carbon, and a layer comprising silica. The amount of sorbent used in the gas filter depends on the analytical application for which the apparatus is intended to be used, and also the amount and configuration of the sorbent in the SPE cartridge. For example, if a large amount of sorbent is used in the SPE cartridge, or if the solution to be analyzed contains an involatile solvent, or an involatile solvent is used to wash the sorbent in the SPE cartridge after the analytes have been adsorbed, it will be necessary to use a larger volume of gas to dry the sorbent in the SPE cartridge than if a small amount of sorbent is used in the SPE cartridge, or if volatile solvents are used. Typically, the amount of sorbent in the gas filter exceeds the amount of sorbent in the SPE cartridge. For example, the weight of sorbent in the gas filter may be, for example more than one times, two times or more, five times or more, ten times or more, or twenty times or more than the weight of sorbent in the SPE cartridge, for example about five times the weight of the sorbent in the SPE cartridge. The amount of sorbent in the air filter typically ranges from about 100 mg to about 100000 mg, preferably 1000 mg to 50000 mg, more preferably, about 4000 mg to 50000 mg, for example 100, 200, 500, 1000, 2000, 4000, 6000, 10000, 20000 or 50000 mg, though these amounts are stated by way of illustration, and are not intended to limit the scope of the invention. Typically, average particle sizes, which are stated by way of illustration, and are not intended to limit the scope of the invention, are in the range of about 5 to about 2000 μm, most typically about 20 to about 500 μm, preferably about 60 to about 210 μm.

The method of the invention uses the above-described apparatus in sample preparation for analysis of liquid phase samples. Starting with a solid phase extraction cartridge and a gas filter as described above, the method comprises first introducing a liquid sample into the SPE cartridge, then passing a liquid sample through the bed of the first sorbent in the solid phase extraction cartridge. With an essentially gastight connection formed between the outlet of the gas filter and the inlet of the solid phase extraction cartridge, a gas is then passed through the connected gas filter and solid phase extraction cartridge such that the gas passes through the bed of the second sorbent in the gas filter before passing through the bed of the first sorbent in the solid phase extraction cartridge to dry the bed of the first sorbent. When the first sorbent is dry, a solvent is passed through the dried bed of the first sorbent in the SPE cartridge to elute any analytes that have been adsorbed onto the sorbent in the SPE cartridge. The solvent is collected after passage through the sorbent bed in the SPE cartridge.

The collected solvent can then be subjected to instrumental analysis to identify and/or quantitate the amount of any analytes which were dissolved in the original liquid sample and which were adsorbed when the liquid sample was passed through the sorbent in the SPE cartridge.

In the above-described method, it is contemplated that in the step of introducing the sample into the SPE cartridge that the sample is introduced into the SPE cartridge directly, and not passed through the sorbent in the gas filter. Therefore, if the solid phase extraction cartridge has only one inlet, forming the connection between the gas filter and SPE cartridge would be performed after the introduction of the sample into the SPE cartridge. However, once the sample has been introduced into the SPE cartridge the sample could be passed through the sorbent bed in the SPE cartridge either before or after the gas filter is connected. For example, the sample could be passed through the sorbent bed of the SPE cartridge before attaching the gas filter for drying. Alternatively, after the sample has been introduced, the gas filter could be attached immediately, prior to passing the sample through the sorbent bed of the SPE cartridge. Similarly, once the SPE cartridge has been dried, it is contemplated that the solvent is passed through the bed of the SPE cartridge directly, and not passed through the sorbent in the gas filter. Otherwise, the solvent could elute impurities that may be adsorbed in the gas filter.

When the method is applied in practice, additional steps may be desirable or required, depending on the particular application to which the method is applied. Such steps could include passing one or more solvents or solutions through the SPE cartridge before passing the liquid sample which is to be analyzed to wash or condition the sorbent in the SPE cartridge, or both. In addition, after passing the liquid sample through the sorbent in the SPE cartridge but before drying, it may be desirable to include a washing step in which the sorbent in the SPE cartridge is washed to remove unadsorbed components of the sample. The solvent used for such a washing step would be selected as one that would not elute the adsorbed analytes of interest from the SPE cartridge, and would typically be the base solvent of the liquid sample (i.e. pure water when an aqueous sample is being analyzed). Also, one or more elution steps may be involved in eluting the analytes from the sorbent in the SPE cartridge; for example, more than one solvent may be used to elute the analytes from the cartridge. In addition, when it is stated that a solvent is passed through the sorbent in the SPE cartridge to elute the analytes from the cartridge, the "solvent" which is used to elute the analytes may be a single pure solvent, a mixture of more than one solvent, or a solution. The solvents or solution which are used to wash or condition the sorbent in the SPE cartridge, or which are used to elute analytes from the sorbent in the SPE cartridge, may be selected by the person skilled in the art as appropriate to the particular application to which the method is applied.

Preferred embodiments of the method of the invention are those where the liquid sample being analyzed is an aqueous sample. The method of the invention is particularly appropriate and particularly advantageous in the analysis of aqueous samples since water is relatively involatile, and therefore, if the sorbent in the SPE cartridge is to be dried using air, a large volume of air may need to be used for the drying. Thus, if the drying were performed without using a gas filter, the risk of contamination of the sorbent in the SPE cartridge would be high, even if contaminants were present in only trace amounts in the air, because of the large volume of air required to be used and the concentrating effect of the SPE cartridge. On the other hand, when the apparatus and method of the invention are used, and a gas filter is employed, the large volume of air required to dry the sorbent in the SPE cartridge in analyzing an aqueous sample does not pose a problem because the air passes through the sorbent in the SPE cartridge only after being purified by passage through the sorbent in the filter.

In addition, there are some applications involving analysis of aqueous samples where the analytes which are of interest are present in very low concentrations. When the analytes are present in very low concentrations, contamination of the sorbent of the SPE cartridge by airborne contaminants introduced during air drying would pose a particularly significant problem because the amount of contaminants introduced from the air may be significant relative to the amount of analytes adsorbed, making the latter more difficult to detect and quantitate with accuracy. Again, the use of the apparatus and method of the invention alleviate this problem.

Examples of applications involving aqueous samples where the apparatus and method of the invention can be advantageously used include analysis of water samples, including analysis of drinking water, environmental water samples such as river water and ground water, and waste water. Other examples include analysis of biological fluids, for example blood and urine testing, particularly testing for substances such as drugs.

In principle, the method of the invention can be used when any gas is used to dry the SPE cartridge if the gas potentially contains an impurity that would be detrimental to the analysis. A particular advantage of the invention is that it permits air, more particularly unpurified air, to be used to dry the sorbent in the SPE cartridge with reduced risk of contamination by airborne contaminants. It is in this respect that the method of the invention is most advantageous. However, even if precautions were taken to supply an inert gas, or purified air to a laboratory in which a sample preparation were conducted, the use of the method of the invention could still be advantageous in that the use of the gas filter apparatus purifies the air immediately before it passes into the SPE cartridge to dry the sorbent of the SPE cartridge. Thus the method guards against contaminants generated in the laboratory itself or on laboratory equipment, from chemicals (which may include standard samples of the analytes of interest) being used in the laboratory, or in an inert gas supply, or tubing used to supply such gas.

In addition to the foregoing, it is noted that passage of gas through the sorbent in the SPE cartridge can be effected by applying a positive pressure of gas at the inlet of the gas filter. Alternatively, the passage of air through the sorbent can be effected by applying suction at the outlet of the SPE cartridge, i.e. at the luer fitting if the syringe-barrel-like preferred embodiment of the SPE cartridge is used, for example by attaching the outlet to a suitable vacuum source, and leaving the inlet of the gas filter open to air. In either case, because of the essentially gastight connection between the inlet of the SPE cartridge and the outlet of the gas filter, essentially all the gas which passes through the bed of sorbent of the SPE cartridge does so only after first being purified by passage through the bed of sorbent in the gas filter.

What is claimed is:

1. A method for sample preparation for analysis of liquid samples comprising:
   providing a solid phase extraction cartridge which comprises a first container having an inlet and an outlet, said first container containing a bed of a first sorbent;
   providing a gas filter which comprises a second container having an inlet, an outlet, and a luer fitting at said outlet, said second container containing a bed of a second sorbent;
   introducing a liquid sample comprising a solvent and one or more analytes into the solid phase extraction cartridge, such that the liquid sample is not passed through the bed of the second sorbent before being introduced into the solid phase extraction cartridge;
   adsorbing the one or more analytes onto the first sorbent and passing the solvent through the bed of the first sorbent;
   forming an essentially gastight connection between the inlet of the solid phase extraction cartridge and the outlet of the gas filter using an adapter so dimensioned as to form a tight fit to the inlet of the solid phase extraction cartridge and receive the luer fitting of the outlet of the gas filter;
   passing a gas through the gas filter and the solid phase extraction cartridge such that the gas passes through the bed of the second sorbent in the gas filter before passing through the bed of the first sorbent in the solid phase extraction cartridge to dry the bed of the first sorbent;
   introducing a second solvent into the solid phase extraction cartridge, such that the second solvent is not passed through the bed of the second sorbent before being introduced into the solid phase extraction cartridge;
   passing the second solvent through the dried bed of the first sorbent to elute the one or more analytes adsorbed to the first sorbent; and
   collecting the second solvent containing the one or more eluted analytes.

2. The method of claim 1, wherein the second sorbent comprises at least one composition selected from the group consisting of silica; bonded silicas; silicates; alumina; activated carbon; graphitized carbon; and ion exchange resins.

3. The method of claim 2, wherein the second sorbent comprises at least one composition selected from the group consisting of magnesium silicate; alumina; unbonded silica; octadecyl bonded silica; octyl bonded silica; ethyl bonded silica; propyl bonded silica, n-butyl bonded silica, isobutyl bonded silica, tertiary butyl bonded silica, pentyl bonded silica, hexyl bonded silica; heptyl bonded silica; n-decyl bonded silica; n-dodecyl bonded silica; eicosyl bonded silica; tricontyl bonded silica; phenyl bonded silica; cyclohexyl bonded silica; cyanopropyl bonded silica; propanediol bonded silica; diethylaminoethyl bonded silica; aminopropyl bonded silica; carboxyethyl bonded silica; propylsulfonic acid bonded silica; ethylbenzene sulfonic acid bonded silica; cyanopropyl bonded silica; and trimethylammonium propyl bonded silica.

4. The method of claim 3, wherein the second sorbent comprises activated carbon.

5. The method of claim 4, wherein the activated carbon is granular activated carbon.

6. The method of claim 1, wherein:
   the bed of the first sorbent is contained in a volume defined by two porous filters positioned between the inlet and the outlet of the solid phase extraction cartridge; and
   the bed of the second sorbent is contained in a volume defined by two porous filters positioned between the inlet and the outlet of the gas filter.

7. The method of claim 6, wherein:
   the first container is a cylindrical tube having a luer fitting at its outlet and one of the porous filters adjacent to its outlet.

8. The method of claim 6, wherein the second container is a cylindrical tube having one of the porous filters adjacent to its outlet.

9. The method of claim 1, wherein the first sorbent comprises at least one composition selected from the group consisting of silica; bonded silicas; silicates; alumina; activated carbon; graphitized carbon; and ion exchange resins.

10. The method of claim 9, wherein the first sorbent comprises at least one composition selected from the group consisting of magnesium silicate; alumina; unbonded silica; octadecyl bonded silica; octyl bonded silica; ethyl bonded silica; propyl bonded silica, n-butyl bonded silica, isobutyl bonded silica, tertiary butyl bonded silica, pentyl bonded silica, hexyl bonded silica; heptyl bonded silica; n-decyl bonded silica; n-dodecyl bonded silica; eicosyl bonded silica; tricontyl bonded silica; phenyl bonded silica; cyclohexyl bonded silica; cyanopropyl bonded silica; propanediol bonded silica; diethylaminoethyl bonded silica; aminopropyl bonded silica; carboxyethyl bonded silica; propylsulfonic acid bonded silica; ethylbenzene sulfonic acid bonded silica; cyanopropyl bonded silica; and trimethylammonium propyl bonded silica.

11. The method of claim 9, wherein the first sorbent comprises a bonded silica.

12. The method of claim 1, wherein the bed of the second sorbent comprises activated carbon and silica.

13. The method of claim 12 wherein the activated carbon is granular activated carbon.

14. The method of claim 12, wherein activated carbon is in a first layer and the silica is in a second layer.

15. The method of claim 1, wherein the gas is air.

16. The method of claim 15, wherein the air is passed through the connected gas filter and solid phase extraction cartridge by applying suction at the outlet of the solid phase extraction cartridge.

17. The method of claim 16, wherein the liquid sample is a water sample, the first sorbent comprises a bonded silica and the second sorbent comprises activated carbon.

18. The method of claim 1, wherein the weight of the sorbent in the gas filter is about two times or more the weight of the sorbent in the solid phase extraction cartridge.

19. The method of claim 18, wherein the weight of the sorbent in the gas filter is about five times or more the weight of the sorbent in the solid phase extraction cartridge.

20. The method of claim 1, wherein the liquid sample is a water sample.

21. The method of claim 1, wherein the gas is passed through the connected gas filter and solid phase extraction cartridge by applying positive pressure of gas at the inlet of the gas filter.

* * * * *